United States Patent [19]

Webb, Jr.

[11] 4,020,415
[45] Apr. 26, 1977

[54] COMBUSTION PRODUCT INDICATOR

[75] Inventor: William Webb, Jr., Denver, Colo.

[73] Assignee: Unitec, Inc., Denver, Colo.

[22] Filed: Dec. 30, 1974

[21] Appl. No.: 537,300

[52] U.S. Cl. .............................. 324/33; 340/237 S
[51] Int. Cl.² .................. G01N 27/62; G08B 17/12
[58] Field of Search .................... 324/33; 340/237 S

[56] References Cited
UNITED STATES PATENTS

| | | | |
|---|---|---|---|
| 3,718,919 | 2/1973 | Sasaki | 340/237 S |
| 3,882,477 | 5/1975 | Muellar | 340/237 S |

Primary Examiner—Palmer C. Demeo
Assistant Examiner—Vincent J. Sunderdick
Attorney, Agent, or Firm—O'Rourke, Harris & Hill

[57] ABSTRACT

A combustion product indicating device for use as a calibration or surveying instrument is disclosed. The device senses the presence of combustion and provides an indication of the same including an indication of the amount of combustion sensed within predetermined limits. An ionization detector is utilized to sense the products of combustion and provide an output indicative thereof, which output is coupled through a field effect transistor to a pair of operational amplifiers, which amplifiers function as followers with the latter amplifier having a reference input that may be varied to adjust the reading of a meter, which meter receives the output from the operational amplifiers. Optional circuitry is also provided for providing a voltage output that varies within predetermined limits and is indicative of the amount of combustion sensed. A method for calibrating combustion detectors is also disclosed.

8 Claims, 1 Drawing Figure

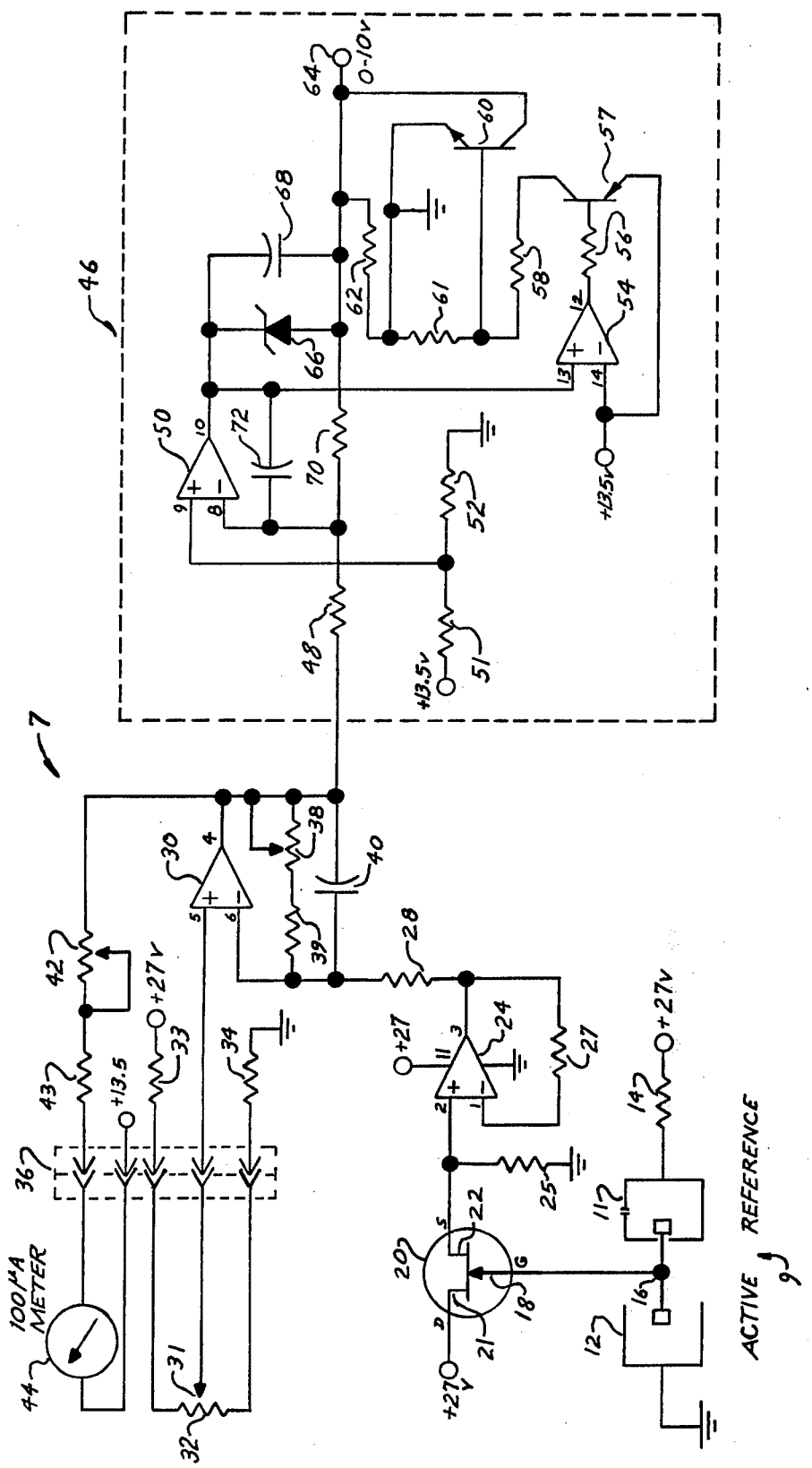

COMBUSTION PRODUCT INDICATOR

FIELD OF THE INVENTION

This invention relates to a combustion product indicator and, more particularly, relates to a calibration or surveying device providing an indication of the amount of combustion sensed within predetermined limits, as well as a method for calibrating combustion detectors.

BACKGROUND OF THE INVENTION

Various types of sensing devices have been developed for monitoring a variety of conditions. One of the more important conditions often monitored is that of combustion with a view toward early discovery of fire to thus minimize loss caused thereby. In monitoring for detection of combustion, it is important that the sensing device be properly adjusted so as to avoid erroneous alarm signals when no undesired combustion is actually sensed, as well as to assure that a signal will be provided where unwanted combustion does actually exist. Equipment for calibrating combustion monitoring devices are thus important to assure proper operation of such devices. In addition, it is sometimes desirable that equipment be provided to survey a location and determine combustion as well as the amount thereof.

Combustion detection devices have been heretofore suggested and/or utilized but such devices have not proved to be completely satisfactory, particularly for sensing combustion and indicating the amount thereof within predetermined limits. In addition, no fully satisfactory device has been suggested for calibrating combustion detection devices or in providing a device suitable for surveying a location and giving an indication of the amount of combustion sensed.

A combustion detection device providing pulsed sensing utilizing an ionization detector is shown, for example, in U. S. Patent application, Ser. No. 314,689, entitled "Ionization Detector Apparatus," filed Dec. 13, 1972, by Ronn H. Mayer and assigned to the assignee of the present invention. Another combustion detection device providing sensing utilizing an ionization detector and providing an alarm indication by shorting the input leads from a power source is shown, again by way of example, in U.S. application, Ser. No. 504,489, entitled "Combustion Detection Device," filed Sept. 9, 1974, by William Webb, Jr., and assigned to the assignee of the present invention. The detector of this invention is usable in calibrating such devices.

SUMMARY OF THE INVENTION

This invention provides an improved combustion product indicating device that is particularly well suited for providing an indication of combustion as well as the amount of combustion sensed within predetermined limits. The device of this invention is, therefore, well suited for calibrating combustion detection devices and providing a method for such calibration, as well as being useful in surveying a location. An ionization detector provides an input to a field effect transistor, the output of which is coupled through a pair of operational amplifiers to an indicating device, such as a meter, and/or to circuitry providing a variable voltage output.

It is therefore an object of this invention to provide an improved combustion product indicating device.

It is another object of this invention to provide an improved combustion product indicating device suitable for providing an indication of the amount of combustion sensed within predetermined limits.

It is another object of this invention to provide an improved combustion product indicating device suitable for use in calibrating combustion detection devices, as well as a method for calibrating combustion detectors.

It is still another object of this invention to provide an improved combustion product indicating device that is suitable for surveying a location and indicating the combustion sensed thereat.

It is still another object of this invention to provide an improved combustion product indicating device that includes an ionization detector, a field effect transistor, and a pair of operational amplifiers the output of which is coupled to an indicator.

It is still another object of this invention to provide an improved combustion product indicating device that includes a meter for indicating the amount of combustion sensed.

It is yet another object of this invention to provide an improved combustion product indicating device that includes circuitry for indicating the amount of combustion sensed by means of a variable voltage.

With these and other objects in view, which will become apparent to one skilled in the art as the description proceeds, this invention resides in the novel construction, combination, and arrangement of parts substantially as hereinafter described and more particularly defined by the appended claims, it being understood that such changes in the precise embodiment of the hereindisclosed invention are meant to be included as come within the scope of the claims.

BRIEF DESCRIPTION OF THE DRAWING

The accompanying drawing illustrates a complete embodiment of the invention according to the best mode so far devised for the practical application of the principles thereof, and in which the single FIGURE is an electrical schematic diagram of the combustion product indicating device of this invention.

DESCRIPTION OF THE INVENTION

Referring now to the drawing, the numeral 7 indicates generally the combustion product indicating device of this invention. An ionization detector 9 is utilized to sense the presence of combustion. Ionization detector 9 includes a pair of radium 226 chambers 11 and 12 (americium 241 could be utilized, if desired). Radium chamber 11 is preferably substantially closed and thus serves as a reference detector, while radium chamber 12 is preferably open to sample, or monitor, the atmosphere surrounding the detector 9. Thus, detector 9 senses the products of combustion present in the atmosphere surrounding the detector and provides an output voltage indicative therof.

Reference chamber 11 is connected at one side to a +27 volt d.c. power supply (not shown) through resistor 14, while active chamber 12 is connected at one side with ground. The output from the detector 9 is taken from the junction 16 between the chambers and is coupled to the input, or gate, 18 of a field effect transistor (FET) 20. In the absence of a sensed fire condition, i.e., under normal operating conditions, the voltage at junction 16 is about +13.0 volts for a zero-meter deflection. Field effect transistor 20, which is preferably a JFET type, serves as a source follower and has the drain electrode 21 connected with the +27 volt power supply (not shown), and the source electrode 22 connected to the positive input of operational amplifier 24 and with ground through resistor 25.

The negative input to operational amplifier 24 is connected with the output of the amplifier through resistor 27, and the output from the amplifier is coupled through resistor 28 to the negative input of operational amplifier 30. The positive input to operational amplifier 30 has a reference input voltage coupled thereto from center tap 31 of potentiometer 32, which potentiometer is connected in series with resistors 33 and 34 between the +27 volt power supply (not shown) and ground as a voltage divider. Potentiometer 32 may be access mounted, as indicated in the drawing, through junction 36. Thus operational amplifier 24 serves as a follower, amplifier 30 is an invertive amplifier with a gain of ≈20, and the positioning of center tap 31 of potentiometer 32 determines the reference voltage applied for setting, or zeroing, the meter 44.

The output of operational amplifier 30 is connected with the negative input of the amplifier through series connection to the potentiometer 38 (a factory adjustment gain control) and resistor 39, and through capacitor 40 connected in parallel with potentiometer 38 and resistor 39. The output from operational amplifier 30 is coupled through series connected potentiometer 42 (a meter range adjustment) and resistor 43 to indicator, or meter, 44 that is access mounted, as through junction 36 as indicated in the drawing. As indicated, meter 44 may be a 100 μmeter connected to a +13.5 volt power supply (not shown).

If desired, optional circuitry 46 may be provided to supply a varying output voltage dependent upon the amount of combustion sensed within predetermined limits. As indicated in the drawing, a voltage output varying between 0 and 10 volts is provided.

The output from operational amplifier 30 is coupled through resistor 48 to the negative input of operational amplifier 50, the positive input to which is coupled from the junction of resistors 51 and 52 connected in series with one another as a voltage divider between the +13.5 volt power supply (not shown) and ground.

The output from operational amplifier 50 is coupled to the positive input of operational amplifier 54, the negative input to which is connected to the +13.5 volt power supply (not shown). The output of operational amplifier 54 is coupled through resistor 56 to the base of transistor 57, the emitter of which is connected to the +13.5 volt power supply (not shown). The output from transistor 57 is connected from the collector through resistor 58 to the base of transistor 60. The base of transistor 60 is connected to ground through resistor 61, while the emitter is directly connected with ground and the collector is connected with ground through resistor 62. The collector of transistor 60 is connected with output junction 64, and it is the purpose of operational amplifier 54 and transistors 57 and 60 to provide a zero reference by pulling the circuit to ground.

The output of operational amplifier 50 is also connected to output junction 64 through Zener diode 66 and capacitor 68 connected in parallel with one another, junction 64 also being connected to resistor 48 through resistor 70, and capacitor 72 is connected in the feedback path of operational amplifier 50.

In operation, potentiometer 32 is adjusted to zero the reading on meter 44, and for calibration purposes, the detector 9 is placed in the same environment with one or more combustion detectors to be calibrated. Using lamp wick or other combustion sources, a controlled amount of products of combustion is injected into the environment. The amount of combustion is such that approximately 1.6 percent per foot of obscuration provides a half deflection (5.0) on meter 44 (meter 44 provides a substantially linear reading and, for example, a 3 percent obscuration causes a 9.0 reading on the meter).

The amount of obscuration injected into the environment surrounding the detector 9 and detector devices to be calibrated is adjusted so that a 4.5 reading is present on meter 44. At this time, any detection device sounding an alarm is adjusted so that no alarm sounds. Thereafter, the amount of injected obscuration is increased so that a meter reading of 5.5 is obtained. At this time, any detection device not sounding an alarm is adjusted to cause the alarm to sound. The detection devices are then calibrated and ready for use. Obviously, other values and settings could be used as desired, and the invention is not meant to be limited to the illustration set forth hereinabove.

For use in surveying, detector 9 is merely placed in the location and meter 44 will indicate the amount of combustion sensed within the range of the meter.

In addition, circuitry 46, if utilized, provides a voltage output varying between 0 and 10 volts that is indicative of the amount of sensed combustion. Thus, circuitry 46 converts a voltage varying between 13.5 volts and 3.5 volts (at the input from operational amplifier 30) into an output voltage of 0 to 10 volts. Thus, the variable voltage output could be used the same as mentioned for meter 44, a 10 volt output being indicative of a full scale deflection (10.0) on the meter.

The following is a list of components utilized in a working embodiment of this invention, it being understood that said components are for illustration purposes only and the invention is not meant to be limited thereto:

| | |
|---|---|
| Field Effect Transistor 20 | - 2N4117A; |
| Transistor 57 | - 2N3906; |
| Transistor 60 | - 2N3904; |
| Zener Diode 66 | - 1N965B; |
| Resistors | - 14–1.5K, 25–1M, 27–100K, 28–10K, 32 (potentiometer)–0–1.5K, 33–4.7K, 34–4.7K, 38 (potentiometer)–0 to 100K, 39–27K, 42 (potentiometer)–0 to 20K, 43–82K, 48–100K, 51–100K, 52–100K, 56–100K, 58–100K, 61–10K, 62–10K, and 70–100K; |
| Capacitors 40 and 72 | - 0.1 MF; and |
| Meter 44 | - 100 μA. |

In view of the foregoing, it is to be appreciated that this invention provides an improved combustion product indicating device that is well suited for indicating the amount of combustion sensed within predetermined limits and is useful for calibration or surveying purposes.

What is claimed is:

1. A combustion product indicating device, comprising: ionization detection means providing an output indicative of products of combustion sensed by said detection means; a field effect transistor for receiving said output from said ionization detection means and providing an output reflective thereof; at least one operational amplifier connected to receive said output from said field effect transistor, said operational amplifier also receiving a reference voltage; and indicator means connected with said operational amplifier and responsive to an output therefrom indicating the amount of products of combustion sensed by said ionization detection means within predetermined limits, said indicator means including circuitry for providing a variable voltage output indicative of the amount of products of combustion sensed by said ionization means with said circuitry including a pair of series connected operational amplifiers, the latter of which is connected with a pair of series connected transistors.

2. The combustion indicating device of claim 1 wherein said device includes a pair of series connected operational amplifies, the former of which receives said output from said field effect transistor and the latter of which receives said reference voltage.

3. The combustion product indicating device of claim 1 wherein said indicating means includes a 100$\mu$meter for indicating the amount of products of combustion sensed by said ionization detection means.

4. The combustion product indicating device of claim 3 wherein said device includes a potentiometer for adjusting said reference voltage supplied to said operational amplifier whereby said meter reading can be adjusted.

5. The combustion product indicating device of claim 4 wherein said meter and potentiometer are access mounted with respect to the remainder of said device.

6. The combustion product indicating device of claim 1 wherein said device is positioned adjacent to combustion detection equipment for calibrating the same.

7. The combustion product indicating device of claim 1 wherein said device is positioned at a predetermined location for surveying the amount of combustion at said location.

8. A combustion product indicating device, comprising: a pair of radioactive chambers defining an ionization detector that provides an output indicative of the products of combustion sensed by said detector; a field effect transistor, the gate of which is connected with said ionization detector to receive the output therefrom, said transistor providing an output at the drain electrode reflective of an output received from said field effect transistor; first and second series connected operational amplifiers, the first of which is connected with said field effect transistor to receive the output therefrom; a reference voltage source having an adjustable control, said reference voltage source providing a reference voltage to said second operational amplifier; a meter connected with said operational amplifiers for indicating the amount of products of combustion sensed by said ionization detector within the limits of said meter; and circuit means providing a variable voltage output responsive to the output from said operational amplifiers, said voltage output being indicative of the amount of products of combustion detected by said ionization detector.

* * * * *